US009276348B1

(12) United States Patent
Vadlamudi et al.

(10) Patent No.: US 9,276,348 B1
(45) Date of Patent: Mar. 1, 2016

(54) LEAD LOCK FOR SECURING A LEAD TO A PULSE GENERATOR

(71) Applicant: DONATELLE PLASTICS, INC., New Brighton, MN (US)

(72) Inventors: Raghu Vadlamudi, Woodbury, MN (US); Matthew L. Iwen, Savage, MN (US); Christopher M. Zerby, New Brighton, MN (US); Clint J. Fonder, Elk River, MN (US)

(73) Assignee: Donatelle Plastics, Inc., New Brighton, MN (US)

( * ) Notice: Subject to any disclaimer, the term of this patent is extended or adjusted under 35 U.S.C. 154(b) by 0 days.

(21) Appl. No.: 14/598,515

(22) Filed: Jan. 16, 2015

(51) Int. Cl.
| H01R 13/625 | (2006.01) |
| H01R 13/453 | (2006.01) |
| A61N 1/02 | (2006.01) |
| H01R 13/52 | (2006.01) |
| H01R 13/20 | (2006.01) |

(52) U.S. Cl.
CPC ............... *H01R 13/453* (2013.01); *A61N 1/02* (2013.01); *H01R 13/20* (2013.01); *H01R 13/5202* (2013.01)

(58) Field of Classification Search
CPC .. H01R 13/453; H01R 13/20; H01R 13/5202; A61N 1/02
USPC ................... 439/345, 350, 346, 347
See application file for complete search history.

(56) References Cited

U.S. PATENT DOCUMENTS

| 4,262,673 | A |  | 4/1981 | Kinney et al. | |
| 6,979,220 | B1 | * | 12/2005 | Ray | H01R 13/6392 439/346 |
| 7,287,998 | B2 | * | 10/2007 | Masai | G03G 21/1652 439/342 |
| 2012/0090161 | A1 |  | 4/2012 | Biggs et al. | |

* cited by examiner

*Primary Examiner* — Khiem Nguyen
(74) *Attorney, Agent, or Firm* — Nikolai & Mersereau, P.A.; Thomas J. Nikolai

(57) ABSTRACT

A connector for electrically and mechanically coupling a lead pin to a pulse generator that includes a housing and a plunger having openings which can be aligned in an unlocked position to permit insertion and retraction of the lead pin. The connector also has a biasing member which moves and then holds the plunger in a locked position relative to the housing such that the housing and plunger pinch the lead pin thereby coupling the lead pin to the connector.

20 Claims, 2 Drawing Sheets

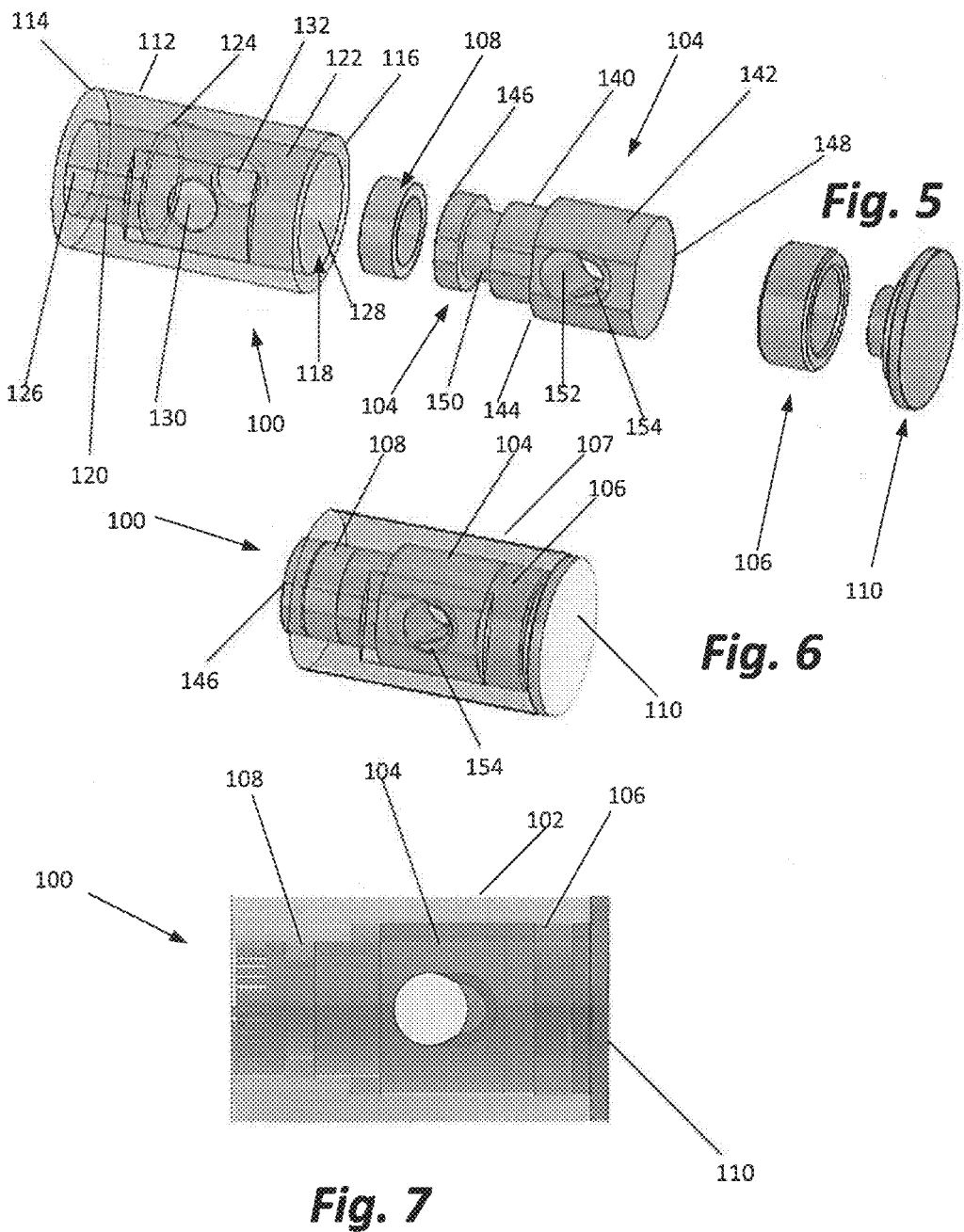

LEAD LOCK FOR SECURING A LEAD TO A PULSE GENERATOR

CROSS-REFERENCED TO RELATED APPLICATIONS

Not applicable.

STATEMENT REGARDING FEDERALLY SPONSORED RESEARCH OR DEVELOPMENT

Not applicable.

BACKGROUND OF THE INVENTION

I. Field of the Invention

The present invention relates to leads, pulse generators and connectors used to couple leads to a pulse generator. More specifically, the present invention concerns locks incorporated in the header of a pulse generator to mechanically and electrically couple a lead to the pulse generator.

II. Discussion of Related Art

For more than a half century, cardiac rhythm management devices including an implantable pulse generator and leads have been used to treat various medical conditions. Implantable cardiac rhythm management devices are now routinely employed as cardiac pacemakers, cardiac defibrillators and cardioverters. Neuromodulation systems, which are similar to cardiac rhythm management systems because they also include a pulse generator and one or more leads, are used to resolve chronic and intractable pain, to ameliorate the symptoms of Parkinson's disease, to relieve incontinence, and to restore hearing. New and exciting frontiers in the field of neuromodulation are currently being explored.

When implantable cardiac rhythm management devices are employed, the pulse generator is implanted at a first location within the body and the lead(s) are extended through the vasculature of the patient's body between the location of the pulse generator and the patient's heart. When implanting a neuromodulation system, the leads extend between the part of the patient's body to be stimulated and the pulse generator.

Pulse generators used for cardiac rhythm management and neuromodulation typically include a header having one of more ports. Leads used in cardiac rhythm management and neuromodulation typically include a lead pin adapted to be mated with a port of the header to form electrical connections between the lead and the pulse generator.

Various standards have emerged concerning the design of the aforementioned ports and lead pins. For example, the International Organization for Standardization has published ISO 27186, a standard entitled "Active Implantable Medical Device—Four-Pole Connector System for Implantable Cardiac Rhythm Management Devices—Dimensional and Test Requirements." When leads and pulse generators conform to this standard leads and pulse generators for cardiac rhythm management from different manufacturers may be used together.

SUMMARY OF THE INVENTION

The present invention concerns self-locking connector blocks which may be employed in the header of a pulse generator to electrically and mechanically couple the lead pin of a lead to the pulse generator. The connector block includes a housing, a plunger and a biasing member.

The housing has a wall structure defining an interior chamber and first and second ends. At least the first end of the housing's wall structure has an opening in communication with the chamber. The housing also has a pair of aligned pin receiver openings in the wall structure. The pin receiver openings are intermediate the first and second ends of the housing and are adapted to permit the distal end of the lead pin to pass through the housing. The housing also has a housing stop surface extending inwardly into the chamber from the wall structure at a location between the pair of aligned pin receiver openings and the first end of the housing.

The plunger has a first section extending between the proximal end of the plunger and a plunger stop surface and a second section extending between the plunger stop surface and the distal end of the plunger. The plunger also includes a pin receiver orifice extending through the second section. The pin receiver orifice is adapted to permit the distal end of the lead pin to pass therethrough. The plunger is located within the chamber of the housing and is movable between a locked position and an unlocked position.

The biasing member is adapted to engage the second section of the plunger to bias the plunger into a locked position. In the locked position, the housing stop surface and the plunger stop surface engage each other and the proximal end of the plunger extends outwardly through the opening in and past the first end of the housing. A lead pin extending through the pin receiver openings of the housing and the pin receiver orifice of the plunger is pinched between surfaces of the housing and the plunger when the plunger is in the locked position.

The plunger will need to move from the locked position to the unlocked position to either insert or remove a lead pin from the self-locking connector block. This is accomplished by pushing (or pulling) the first end of the plunger toward the second end of the housing with sufficient force to overcome the force of the biasing member and move the plunger. When in the unlocked position, the plunger and housing no longer pinch any lead pin coupled to the connector with sufficient force to hold the lead pin in the connector. The lead pin is then extracted from the connector.

The housing, plunger and biasing member may have various other features. For example, the housing may have a second opening in the second end to permit the plunger to be placed in the housing. This opening may be sealed with a cap. The housing may be made of metal or made of an electrically conductive plastic material. The housing's stop surface may be the result of a difference in the thickness of the wall structure between the first end or second end of the housing or by the housing otherwise being stepped.

The plunger may also be made of an electrically conductive material such as metal or a conductive plastic. The plunger may also include a structure adapted to be received within and engage a surface of a groove located in the surface of the lead pin. In accordance with the standard referenced above, lead pins are provided with such a groove in the reduced diameter portion adjacent the distal end of the lead pin. The first section of the plunger may also have a channel for receiving a seal. A seal in the form of a ring surrounding a portion of the first section of the plunger may be provided. Silicone is one suitable material for forming such a seal.

The biasing member may be a spring made of a suitable material. Alternatively, the biasing member may be a ring formed of a resilient and compressible material. The biasing member may also be made of a shape memory material such a nitinol. The biasing member may also be made of an electrically conductive material.

BRIEF DESCRIPTION OF THE DRAWINGS

The features and attributes which may be employed to practice the present invention will be better understood from a review of the detailed description provided below in conjunction with the accompanying drawings.

FIG. 5 is an exploded perspective view of a self-locking connector block made in accordance with the present invention.

FIG. 6 is an assembled perspective view of the connector block of FIG. 5.

FIG. 7 is a side view of the connector block of FIG. 5.

DETAILED DESCRIPTION

Figure 1:
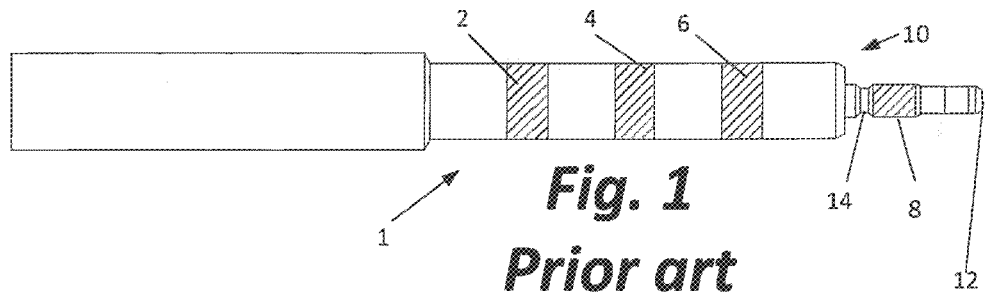
FIG. 1 is a side view of a lead pin in the prior art.

This description of the preferred embodiment is intended to be read in connection with the accompanying drawings, which are to be considered part of the entire written description of this invention. In the description, relative terms such as "lower", "upper", "horizontal", "vertical", "above", "below", "up", "down", "top" and "bottom", "under", as well as derivatives thereof (e.g., "horizontally", "downwardly", "upwardly" "underside", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "joined", and "joining" are used interchangeably and refer to one structure or surface being secured to another structure or surface or integrally fabricated in one piece unless expressly described otherwise.

Figure 2:
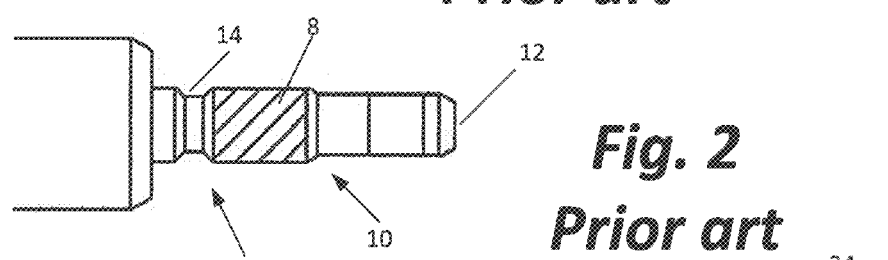
FIG. 2 is a side view of the distal end of the lead pin of FIG. 1.

FIGS. 1 and 2 show a lead pin 1 made in conformance with the aforementioned standard. The lead pin 1 has four electrodes 2, 4, 6 and 8 spaced from each other along the length of the lead pin 1. The lead pin 1 also has a reduced diameter portion 10 at its proximal end 12. The reduced diameter portion 10 includes a groove 14.

Figure 3:
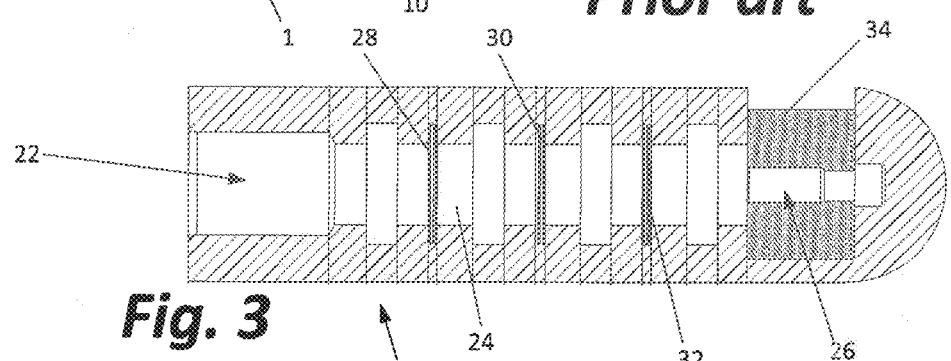
FIG. 3 is a cross-sectional view of a prior art lead pin port of a header used to couple the lead pin of FIG. 1 to a pulse generator.
Figure 4:
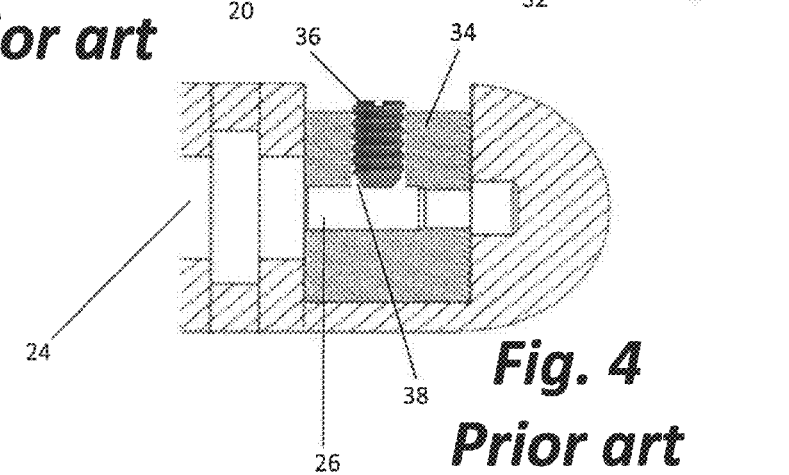
FIG. 4 is a cross-sectional view of the distal end of the port of FIG. 3 showing a prior art connector block and set screw.

FIGS. 3 and 4 show a header 10 having a port 22 for receiving the lead pin 1. The port has a larger diameter section 24 and a reduced diameter section 26. The larger diameter section has electrodes 28, 30 and 32. The reduced diameter section 26 is typically in the form of a metal connecting block 34. When the pin 1 is inserted into the port 22, lead electrode 2 forms an electrical connection with port electrode 28, lead electrode 4 forms an electrical connection with port electrode 30 and lead electrode 6 forms an electrical connection with port electrode 32. Likewise, lead electrode 8 forms an electrical connection with the metal connecting block 34. Seals (not shown) are disposed between these electrical connections to isolate the connections from each other.

Various mechanisms have been employed to ensure a suitable mechanical connection is maintained between the pin 1 and header port 22. Most typically, and almost universally, this mechanical connection is made by tightening one or more set screws such as set screw 36 passing through block 34 against the reduced diameter portion at the distal end 12 of the lead pin 1. A plug (not shown) is then inserted over the set screw 36 in the channel 38 to prevent body fluids from infiltrating. Extremely close tolerances are required when constructing the plug and channel to ensure infiltration does not occur.

While the use of a set screw 36 is generally effective when care is taken to turn the set screw to the proper depth, issues will arise if the set screw is either turned too tight or not tight enough. If the screw is too loose, the lead pin 1 may actually decouple from the port or partially decouple from the port such that the aforementioned electrical connections are lost. If the set screw is turned too tight, damage to the header of the pulse generator or to the lead will occur. As such, special tools such as a torque limited screw driver or wrench are typically employed when tightening the set screw. Also, such screws have inadvertently loosened over time. Likewise, the seals have, at times, failed.

Various attempts have been made to overcome at least some of the foregoing problems by replacing the set screw with some other locking mechanism. One example is provided by U.S. Patent Publication No 2012/0090161 A1 of James c. Biggs et al published Apr. 19, 2012 which discloses a lead lock including a plurality of apertures with inwardly-tapered collet members disposed about the apertures, and a lock screw engagable with threaded anchors to constrict the collet members within the bores to lock in place leads inserted into the bores. However, this arrangement adds substantially to the complexity of coupling and decoupling the lead and pulse generator.

Those skilled in the art will recognize that eventually, and typically as a result of battery depletion, the original pulse generator will need to be replaced. Advantageously, the new pulse generator will be coupled to the existing, already implanted, lead system. Thus, any locking mechanism employed must readily permit this to occur.

FIGS. 5-7 show a self-locking connector 100 which may be employed as a replacement for the block 34 and set screw 36 of FIGS. 3 and 4. The self-locking connector 100 includes a housing 102, a plunger 104 and a biasing member 106. Also shown is a seal 108 and an end cap 110.

The housing 102 is preferably made of an electrically conductive and biocompatible material. The material may be a metal such as titanium or stainless steel. Alloys such as S316L, and MP35N may be employed. The material may also be a ceramic or plastic which is electrically conductive or which is embedded with electrically conductive particles such that the housing will conduct electrical signals passing between the pulse generator and an attached lead.

The housing 102 has a wall structure 112 having two ends 114 and 116. While the housing 102 has a round cylindrical shape, alternative shapes may be employed without deviating from the invention. The wall structure 112 surrounds a chamber 118. The chamber 118 has a first section 120 and a second section 122 separated by a stop surface 124. While the drawings show stop surface 124 being the result of a difference between the inner diameter of the first section 120 and the inner diameter of second section 122, stop surface 124 may be formed in other ways. The stop surface 124 must extend inwardly into the chamber from the wall structure. The drawings simply show one of several ways to form such a stop surface.

As best shown in FIG. 5, the housing 102 has four openings. These include an opening 126 through the end 114, an opening 128 through the end 116 and a pair of aligned pin receiver openings 130 and 132 extending through the wall structure 112. These openings are adapted to permit the distal end of a lead pin (e.g., distal end 12 of lead pin 1) to pass through the wall structure 112 of the housing 102.

The plunger 104 is likewise made of an electrically conductive, biocompatible material such as a suitable metal conductive ceramic or plastic, or a plastic or ceramic embedded with conductive particles. The plunger 104 has a first section 140 and a distal section 142 separated by a stop surface 144. The first section 140 extends between the proximal end 146 and the stop surface 144. The second section 142 extends between distal end 148 and stop surface 144. While the stop surface 144 shown is formed by providing the first section 140 and the second section 142 with different diameters, the stop surface 144 may be formed in other ways. The plunger 104 may also be provided with a recess or channel 150 which retains the seal 108. The plunger 104 also includes a pin receiver orifice 152 which is adapted to allow the distal end of a lead pin (e.g., distal end 12 of the lead pin 1 shown in FIG. 2) to pass through the plunger 104. The plunger 104 may also include a ridge or similar structure 154 extending into the pin receiver orifice 152. The structure 154 is adapted to be received within a channel such as channel 14 of lead pin 1.

The biasing member 106 shown in the drawings is a resilient, compressible elastic ring. The biasing member 106 may alternatively be in the form of a compressible coil spring. The seal 106 may be made of a medical grade silicone or any other suitable material. The end cap 110 is preferably made of an electrically conductive material. As further illustrated in the drawings, when the self-locking connector 100 is assembled, the plunger 104 is located within the chamber 118 of housing 102. The shape of the chamber 118 and the plunger 104 are such that the plunger 104 is able to reciprocate back and forth within the chamber 118 between a locked position and an unlocked position. Before the plunger 104 is inserted into the housing 102, the seal 108 is slid over end 146 and into groove 150. After the plunger 104 is inserted, the biasing member 106 is inserted and the cap 110 is applied to cover opening 158 through which the seal 108, plunger 104 and biasing member 106 were inserted.

The biasing member 106 biases the plunger toward the locked position. The locked position is illustrated in FIG. 6. When in the locked position, the proximal end 146 extends from the chamber 118 through opening 126 in the end 114 of the housing 102. The stop surface 144 of the plunger 104 engages the stop surface 124 of the housing 102, and the pair of aligned pin receiver openings 130 and 132 of the housing 102 is slightly offset from the pin receiver orifice 152 of the plunger 104. Thus, the biasing member 106, the plunger 104 and the housing 102 cooperate to pinch and thereby retain any lead pin having its distal end extending through the pin receiver openings 130 and 132 and orifice 152 of the self-locking connector. When the lead pin has a recess or groove such as 14 shown in FIGS. 1 and 2, and the plunger 104 has a ridge or similar structure 154, the structure 154 resides in the groove when the plunger is in the locked position.

Unlocking the self-locking connector 100 may be achieved by squeezing or otherwise pushing on the end 146 of the plunger 104 with sufficient force to overcome the force exerted by the biasing member to more the plunger 140 in the direction of cap 110. When the pin receiver orifice 152 is aligned with the pin receiver openings 130 and 132, the distal end of a pin (such as distal end 12 of pin 1) may be inserted into or retracted from the self-locking connector. As soon as such squeezing or pushing force is removed, the biasing member returns the plunger to the locked position.

Various modifications may be made without deviating from the invention. For example, the entire self-locking connector described above may be encapsulated in the header if the material of the header is pliable enough to permit unlocking of the mechanism. In this case, the seal 108 may be eliminated. Alternatively, the end 114 may be left exposed, in which case seal 108 serves to prevent body fluids from infiltrating the header through the exposed portion, while allowing the plunger 104 to be pushed from the locked to unlocked position.

Further, the shapes of the chamber 118 of the housing 102 and plunger 104 may be varied so long as they are adapted to operate as described above. As noted above, the biasing member may be of many different configurations so long as it biases the plunger toward the locked position with sufficient force to capture and hold a lead pin inserted through the aligned opening of the housing and the orifice of the plunger.

Further, the mechanism employed to overcome the force of the biasing member 106 may be something other than a tool or hand of a physician pushing against the end 146 of the plunger 104. If, for example, the plunger 104 is made of a ferrous material, a magnet may be aligned with the plunger 104 such that the magnetic field pushes (or pulls) on the plunger 104 with sufficient force to overcome the force of the biasing member 106 and move the plunger 104 to the unlocked position.

Further still, the biasing member could be made of a temperature-responsive shape memory material such as nitinol. At body temperature (approximately 98.6° F.), the biasing member may have a first shape which holds the plunger 104 in the locked positions. At some other temperature (e.g., room temperature)(approximately 72° F.)), the biasing member made of nitinol may change to a different shape unlocking the plunger 104 and enabling the plunger to move to an unlocked position.

Any of these mechanisms offer substantial advantages over current connector blocks. The risks associated with improper tightening of a set screw are eliminated. The need to seal the access allowing manipulation of the set screw is eliminated. Instead, the entire header may be formed with no openings other than the lead ports and openings permitting conductors to pass between the header and the circuitry inside the body of the pulse generator.

The foregoing description is intended to explain the various features and advantages, but is not intended to be limiting. The scope of the invention is defined by the following claims which are also intended to cover a reasonable range of equivalents.

What is claimed is:

1. For locking to a pulse generator to a lead pin having a proximal end, a self-locking connector block comprising:
   a. a housing having a wall structure defining an interior chamber, a first end, a second end, a pair of aligned pin receiver openings in the wall structure intermediate the first end and the second end and adapted to permit the proximal end of a lead pin to pass therethrough, and a housing stop surface extending inwardly into the chamber from the wall structure at a location between the pair of aligned pin receiver openings and the first end;
   b. a plunger movable within the chamber of said housing between a locked position and an unlocked position, said plunger having a first section extending between a proximal end and a plunger stop surface, a second section extending between said plunger stop surface and a distal end, an pin receiver orifice extending through said second section and adapted to permit the proximal end of a lead pin to pass therethrough;
   c. a biasing member adapted to engage the second section of the of the plunger to bias the plunger into the locked position wherein said housing stop surface and said plunger stop surface engage each other.

2. The self-locking connector block of claim 1 wherein said first end of the housing has an opening in communication with the chamber and said proximal end of said plunger extends through said opening of the first end of the housing past the first end of the housing when the plunger is in the locked position.

3. The self-locking connector block of claim 2 further comprising and opening in the second end of the housing and a cap for sealing the opening in the second end.

4. The self-locking connector block of claim 1 further including a front seal surrounding a portion of the first section of the of the plunger.

5. The self-locking connector block of claim 1 wherein the housing, plunger and biasing member pinch the reduced diameter portion of a lead pin having its distal end inserted through the pair of aligned pin receiver openings in the housing and the pin receiver orifice of the plunger when the plunger is in the locked position.

6. The self-locking connector block of claim 2 wherein the plunger is moved from the locked position to the unlocked position by pushing the first end of the plunger toward the second end of the housing with sufficient force to overcome the force of the biasing member.

7. The self-locking connector block of claim 1 wherein said plunger further comprises a structure adapted to be received within and engage a surface of a groove located in the reduced diameter portion adjacent a distal end of the lead pin.

8. The self-locking connector block of claim 7 wherein said structure adapted to be received within and engage a surface of the groove is a ridge extending inwardly from the edge of the plunger's pin receiver orifice and the center of the plunger's pin receiver orifice.

9. The self-locking connector block of claim 1 wherein said housing is made of an electrically conductive material.

10. The self-locking connector block of claim 1 wherein said plunger is made out of an electrically conductive material.

11. The self-locking connector block of claim 1 wherein said biasing member is a spring made of a conductive material.

12. The self-locking connector block of claim 1 wherein said biasing member is a ring made of a resilient material.

13. The self-locking connector of claim 12 wherein the biasing member is made of silicone.

14. The self-locking connector block of claim 4 wherein the front seal is made of silicone.

15. The self-locking connector block of claim 4 wherein said first section of said plunger has a channel for receiving said front seal.

16. The self-locking connector block of claim 1 wherein the housing stop surface results from a difference in the thickness of the wall structure between the first end and the second end of the housing.

17. The self-locking connector block of claim 1 wherein said plunger is adapted to be moved from its locked position to its unlocked position by applying a magnetic force sufficient to overcome the force of the biasing member.

18. The self-locking connector block of claim 1 wherein said biasing member is made of a shape memory material.

19. The self-locking connector block of claim 18 wherein said shape memory material temperature responsive.

20. The self-locking connector block of claim 18 wherein said shape memory material is nitinol.

\* \* \* \* \*